United States Patent [19]

Cantwell et al.

[11] Patent Number: 5,163,553
[45] Date of Patent: Nov. 17, 1992

[54] SCALPEL BLADE EXTRACTOR AND DISPOSAL UNIT

[76] Inventors: Jay S. Cantwell, 3905 Avery Place Ct., Bridgeton, Mo. 63044; William R. Burkett, 6718 Dale Ave., St. Louis, Mo. 63139

[21] Appl. No.: 777,590

[22] Filed: Oct. 16, 1991

[51] Int. Cl.⁵ ............................................. A61B 19/02
[52] U.S. Cl. .................................. 206/355; 206/363; 81/488
[58] Field of Search ............... 206/354, 355, 356, 358, 206/359, 360, 363, 370; 30/40.2, 40, 339, 123; 29/239, 178; 81/488

[56] References Cited

U.S. PATENT DOCUMENTS

| | | | |
|---|---|---|---|
| 3,244,317 | 4/1966 | Raybin | 206/355 X |
| 4,106,620 | 8/1978 | Brimmer et al. | 206/363 |
| 4,168,777 | 9/1979 | Gaskell et al. | 206/359 |
| 4,180,162 | 12/1979 | Magney | 206/363 |
| 4,270,416 | 6/1981 | Thompson | 81/3 R |
| 4,344,532 | 8/1982 | Eldridge, Jr. et al. | 206/370 |
| 4,386,457 | 6/1983 | Coombs | 29/235 |
| 4,395,807 | 8/1983 | Eldridge, Jr. et al. | 29/239 |
| 4,466,539 | 8/1984 | Frauenhoffer | 206/370 |
| 4,730,376 | 3/1988 | Yamada | 29/239 |
| 4,746,016 | 5/1988 | Pollak et al. | 206/356 |
| 4,903,390 | 2/1990 | Vidal et al. | 29/239 |
| 4,922,614 | 5/1990 | Machida | 30/339 |
| 4,998,334 | 3/1991 | Pemberton et al. | 29/239 |

Primary Examiner—Paul T. Sewell
Assistant Examiner—Jacob K. Ackun, Jr.
Attorney, Agent, or Firm—Grace J. Fishel

[57] ABSTRACT

A scalpel blade extractor and disposal unit formed of semi-flexible plastic material. The unit has a substantially closed chamber within which a blade mounted on a handle is received. The chamber has a top and a bottom and an abutment shoulder is attached to the top and extends below the plane of the bottom for the purpose of retaining the blade in the chamber. A mechanism is provided for increasing the distance between the top and the bottom so that the blade on the handle passes under the abutment shoulder. The bottom has a groove and shoulders around the groove for prying the heel of the blade up such that it is stopped by the abutment shoulder when the handle is withdrawn leaving the blade behind in the chamber.

7 Claims, 3 Drawing Sheets

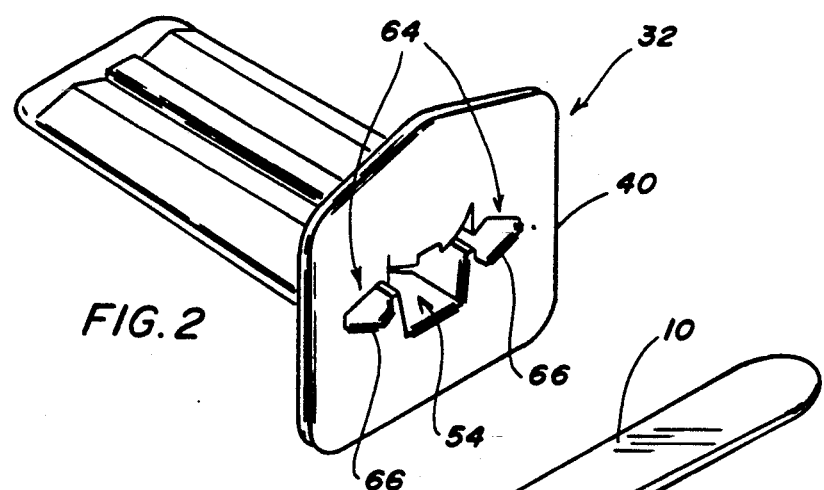
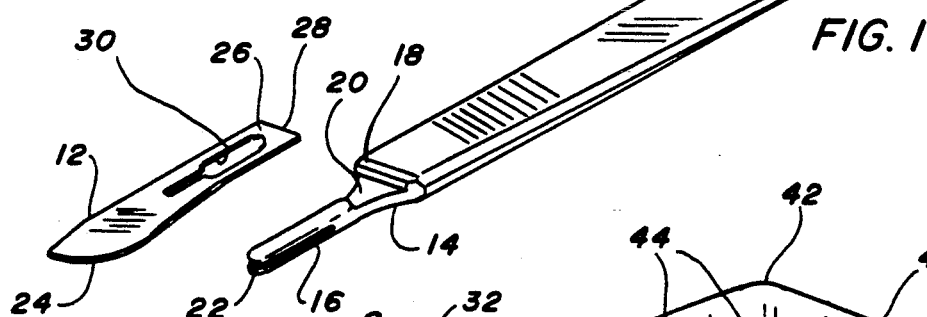
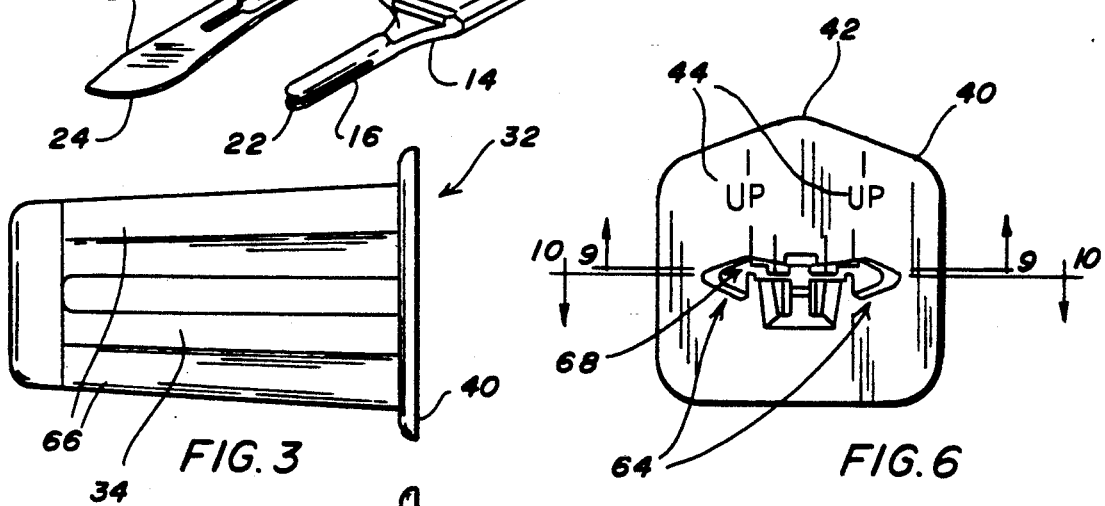
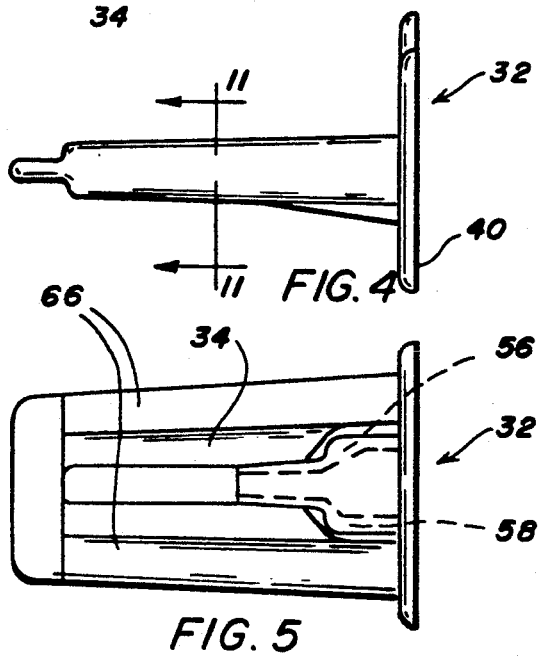
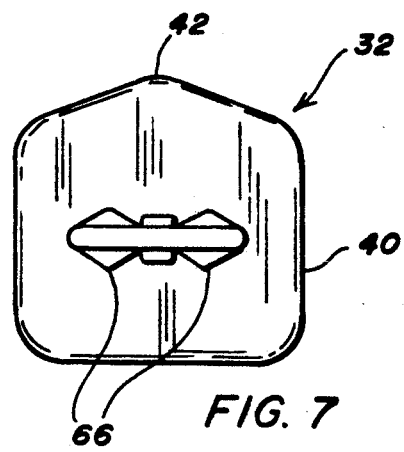

SCALPEL BLADE EXTRACTOR AND DISPOSAL UNIT

The present invention relates to a unit device for extracting a scalpel blade from a handle and for storing the used blade.

BACKGROUND OF THE INVENTION

Disposable surgical scalpel blades are commercially available in several sizes and styles. In use, the blades are supplied by various manufacturers in sterile packaging and are attached to a reusable handle having a tang on which the replaceable blade is mounted. The handle is sterilized between uses and the blade is discarded. Frequently several blades are fitted on the same handle during a procedure as they become dull or contaminated or as a different size or style of blade is needed.

To remove the blade from the handle, the heel of the blade is pried away from the tang with fingers or with a pair of forceps. This task is usually assigned to an operating room nurse. When the scalpel is wet, the forceps or the nurse's fingers may slip and she may be accidentally cut. Not infrequently, the blade will break and fly across the room and each blade (or its parts) must be accounted for before an incision is closed. The dangers associated with these problems are evident.

A number of devices have been proposed for removing a scalpel blade from a handle. Some of the prior art devices are sized for use with a particular size or style of blade and hence require stocking a number of different devices to handle the range of blades normally used during a procedure. Others cannot be used in a surgical field because they are so mechanically complicated that they cannot be readily sterilized. Those which provide storage are usually designed to hold a number of blades which complicates accounting.

In view of the above, there is need for a simple device for removing a wide range of different sizes and styles of scalpel blades that can be readily sterilized, facilitates the removal of the blade with increased safety and provides a reliable method for accounting for each blade.

OBJECTS AND SUMMARY OF THE INVENTION

It is an object of the present invention to provide a simple, inexpensive unit device for extracting a scalpel blade from a handle and for storing the used blade such that it can be properly accounted for and disposed of. Another important object is to provide a scalpel blade extractor and disposal unit that is useful with a wide range of different sizes and styles of scalpel blades and that can be sterilized. Other objects and features of the invention will be in part apparent and in part pointed out hereinafter.

In accordance with the invention, a blade extractor and disposal unit for removing a surgical scalpel blade includes a substantially closed chamber formed of a semi-flexible material. The chamber has a top and a bottom with the distance between the top and the bottom substantially equal to the thickness of the blade.

The bottom of the chamber has sides and ends and a length and width exceeding that of the blade. A groove, opening from one end, is provided in the bottom of the chamber. The groove has a width greater than the width of the tang of scalpel and less than the width of the blade and a depth greater than the thickness of the tang at the open end of the groove.

An abutment shoulder is attached to the top. The abutment shoulder is positioned behind the heel of the blade and extends below the plane of the bottom.

A means for increasing the distance between the top and the bottom of the chamber is provided for opening the chamber from the open end of the groove.

The invention as summarized above comprises the constructions hereinafter described, the scope of the invention being indicated by the subjoined claims

BRIEF DESCRIPTION OF THE DRAWINGS

In the accompanying drawings, in which one of various possible embodiments of the invention is illustrated, corresponding reference characters refer to corresponding parts throughout the several views of the drawings in which:

FIG. 1 is an exploded perspective view of a surgical scalpel blade and a handle to which the blade attaches;

FIG. 2 is a perspective view of a scalpel blade extractor and disposal unit in accordance with the present invention;

FIG. 3 is a top view of the scalpel blade extractor and disposal unit;

FIG. 4 is a side elevational view of the scalpel blade extractor and disposal unit;

FIG. 5 is a bottom view of the scalpel blade extractor and disposal unit;

FIG. 6 is a front end view (right-hand end view as viewed in FIG. 4) of the scalpel blade extractor and disposal unit;

FIG. 7 is a rear end view (left-hand end view as viewed in FIG. 4) of the scalpel blade extractor and disposal unit;

DETAILED DESCRIPTION OF THE INVENTION

Figure 8A:
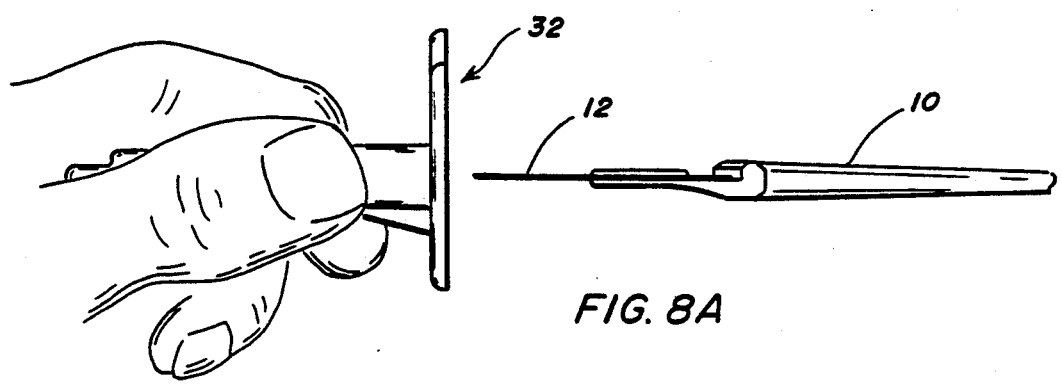
FIG. 8A is a side elevational view of a scalpel blade attached to a handle in process of being inserted into the scalpel blade extractor and disposal unit.

Referring to the drawings and more particularly to FIG. 1, a typical surgical scalpel includes a handle 10 and a removable blade 12. Handle 10 terminates in a laterally convergent intermediate region 14 which narrows into a forwardly extending, relatively long, thin tang 16. On one side of handle 10, intermediate region 14 has an angled surface 18 which slopes downwardly forming a planar recess 20 between handle 10 and an upwardly projecting portion of tang 16. A longitudinal groove 22 is provided on each side of tang 16, starting at its front edge and running for more than half its length.

Blade 12 has a forward sharpened edge 24 and a rearward heel 26. Heel 26 terminates in a back edge 28 which is angled to abut angled surface 18 of handle 10. Blade 12 has a centrally located opening 30 extending through the blade which narrows toward the front of the blade.

In order to mount blade 12 on handle 10, grooves 22 on opposite sides of tang 16 slidably engage the edges of opening 30 at its wide end. Tang 16 is then slidably moved with the aid of grooves 22 to the forward most, narrow portion of opening 30. During the sliding operation, blade 12 is somewhat lifted and distorted from it planar configuration. As the upraised portion of tang 16 fits within opening 30, heel 26 of blade 12 snaps down into recess 20. Blade 12 is locked onto handle 10 because the narrow portion of opening 30 is narrower than the width of tang 16 and the back edge 28 of blade 12 abuts angled surface 18 of handle 10.

To remove blade 12 from handle 10, heel 26 must be pried upward such that the side of blade 12 resting against planar recess 20 is raised slightly above the level of angled surface 18. During this operation (like when the blade is installed), blade 12 is somewhat distorted from its planar configuration. Blade 12 or handle 10 are then slid relative to each other until tang 16 is removed from the narrower portion of opening 20 and the blade is free.

Turning now to FIGS. 2-10, a blade extractor and disposal unit 32 in accordance with the present invention includes a substantially closed chamber 34 for holding blade 12. In the embodiment illustrated in the drawings, unit 32 comprises a flattened sleeve having first and second ends 36, 38, respectively. Unit or sleeve 32 is closed at first end 36 and has a flange 40 at its second end 38. Flange 40 comprises a generally rectangular member and performs the important function of shielding the fingers of a user during a blade removal operation. One side of flange 40 may serve as a pointer 42 for indicating the "up" position in which the unit should be held. Indicia 44 such as the letters UP can also be provided on flange 40.

Conveniently, unit 32 is formed of synthetic plastic materials, produced by injection molding. The nature of the material and thickness of the plastic is such that the unit is semi-flexible. The plastic material may be transparent so that a user may see the used blade or an appropriately located window(s) may be formed in the unit.

Chamber 34 has a top 46 and a bottom 48 with the distance between the top and the bottom substantially equal to the thickness of the blade. Bottom 48 has sides 50 and ends 52 and a length and width exceeding that of blade 12. As illustrated, sides 50 include integrally formed short side flanges within which top 46 fits.

Figure 10:
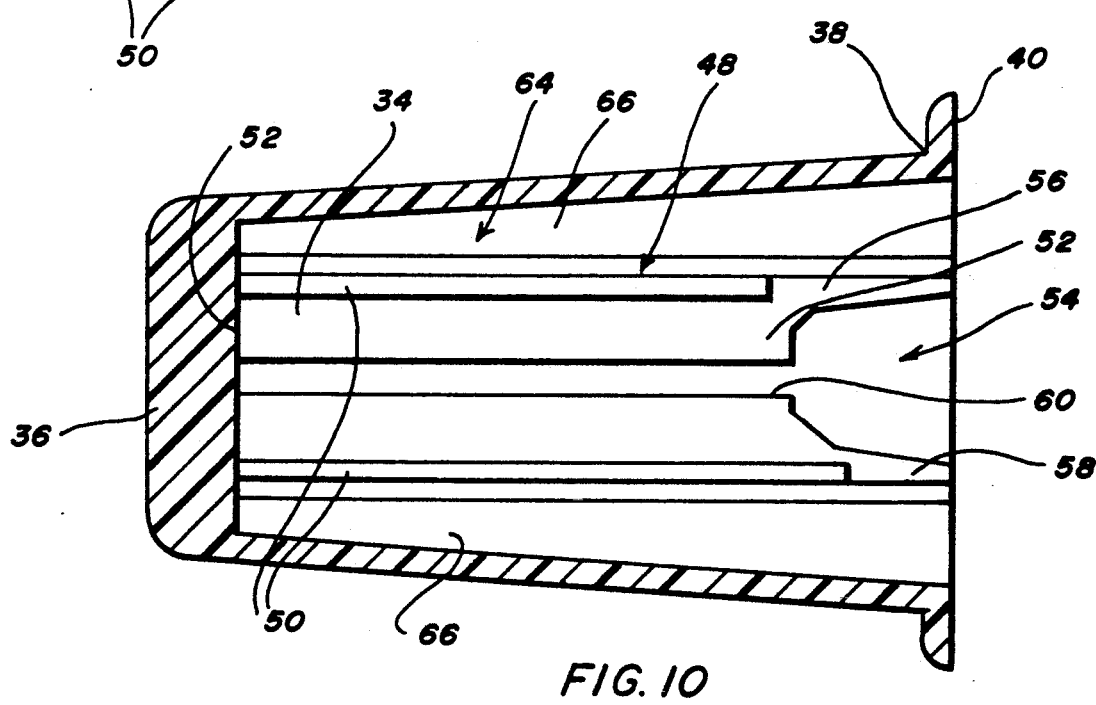
FIG. 10 is a sectional view taken along line 10—10 in FIG. 6.

Chamber 34 is preferably recessed at 54 in unit or sleeve 32 and bottom 48 thickened. As shown in FIG. 10 and in dotted lines in FIG. 5, the sidewalls of recess 54 are laterally convergent and are dimensioned to receive handle 10. They are also asymmetric to fit angled surface 18 so that heel 26 of blade 12 rests on shoulders 56, 58 formed by bottom 48.

A groove 60 is formed in the bottom of chamber 34 opening into recess 54. Groove 60 has a width greater than the width of tang 16 and less than the width of blade 12 and a depth greater than the thickness of tang 16 at the open end of the groove.

An abutment shoulder 62 is attached to top 46 and is preferably set at an angle complementary to angled surface 18 and heel 26 of blade 12. Abutment shoulder 62 is positioned behind heel 26 of blade 12 and extends below the plane of bottom 48.

A means 64 is provided for increasing the distance between top 46 and bottom 48 of the chamber so that blade 12 attached to tang can pass under abutment shoulder 62 into chamber 34. In the embodiment illustrated, central chamber 34 is flanked by a pair of side chambers 66. Each of side chambers 66 has an open side 68 that is connected along one edge to top 46 and at the opposite edge to bottom 48. Chambers 66 (illustrated as triangular) are configured such that when they are compressed in the direction of central chamber 34, open side 68 expands in length causing the distance between top 46 and bottom 48 to increase.

Figure 8B:
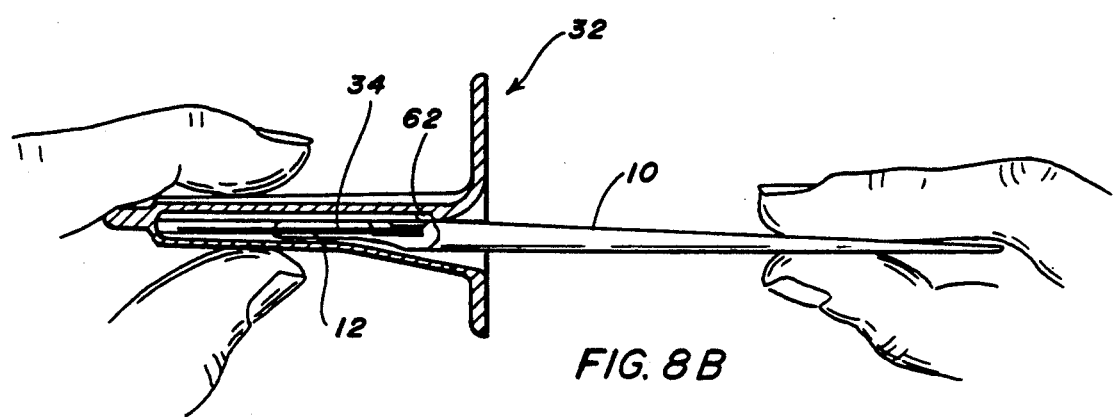
FIG. 8B is like FIG. 8A but in section to show details and with the insertion of the blade completed.

Removal of a used blade 12 from a scalpel handle 10 is accomplished as shown in FIGS. 8A through 8D. As shown in FIG. 8A, scalpel handle 10 with blade 12 attached is inserted into unit 32. Entry of blade 12 under abutment shoulder 62 is accomplished by squeezing on side chambers 66. As side chambers 66 are squeezed, the distance between top 46 and bottom 48 of central chamber 34 is increased. At this point, as shown in FIG. 8B, blade 12 on handle 10 passes under abutment shoulder 62 and is received in central chamber 34.

Figure 8C:
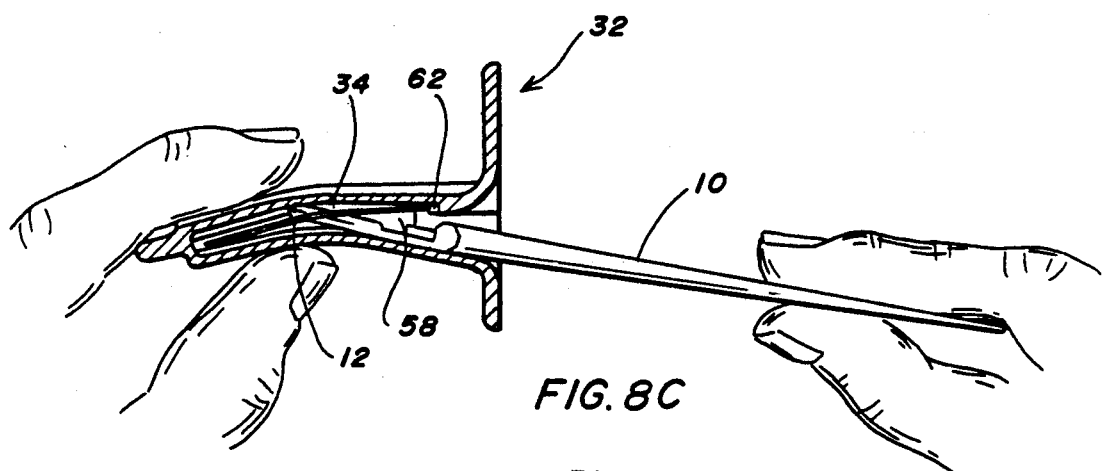
FIG. 8C is like FIG. 8B showing the blade being flexed.
Figure 8D:
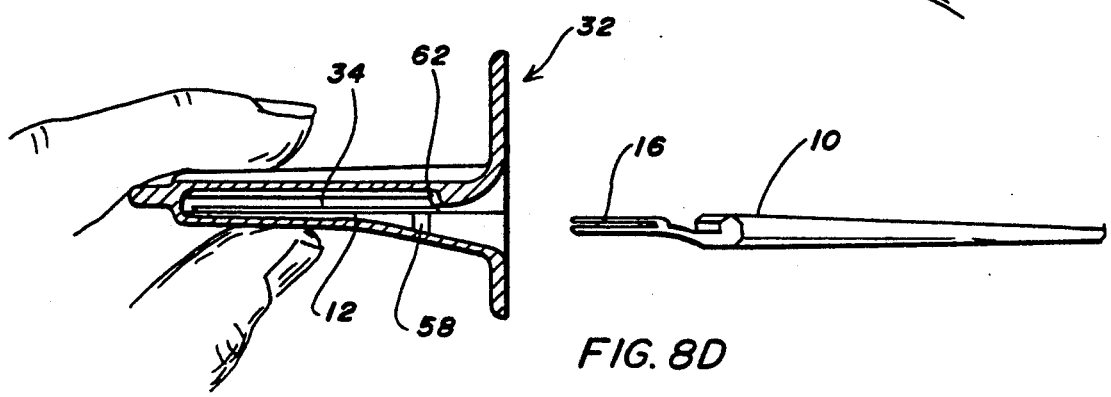
FIG. 8D is like FIG. 8B showing the handle pulled away from the blade with the blade remaining inside of the scalpel blade extractor and disposal unit.
Figure 9:
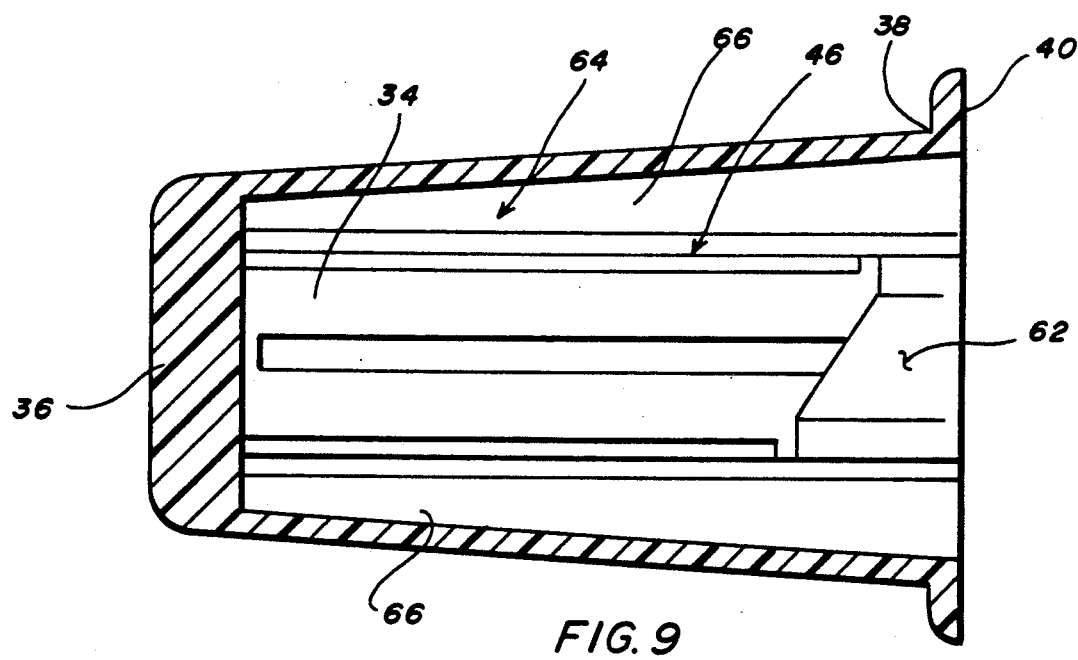
FIG. 9 is a sectional view taken along line 9—9 in FIG. 6.
Figure 11:
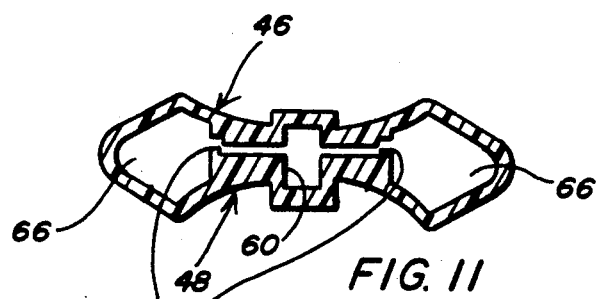
FIG. 11 is a sectional view taken along line 11—11 in FIG. 4.

Turning now to FIG. 8C, the forward most end of blade 12 is squeezed between top 46 and bottom 48 while tang 16 is pressed down into groove 60 by manipulating handle 10. As tang 16 is pressed down, heel 26 is lifted out of planar recess 20 by shoulders 56 and 58 and blade 12 flexed. As handle 10 is pulled away from recess 54, blade 12 is carried along until back edge 28 of heel 26 engages abutment shoulder 62. Continued movement of handle 10 as shown in FIG. 8D, strips blade 12 away from tang 16 and leaves it behind in unit 32 for disposal. Blade 12 is trapped in central chamber 34 (between top 46, bottom 48, flanges on sides 50, closed end 36 and abutment shoulder 62) so that the used blade cannot accidentally fall out of the unit.

As will be observed from FIGS. 8A through 8D, unit 32 detaches scalpel blade 12 from handle 10 without the necessity of touching the blade by hand, thereby permitting the operation to be conducted with increased safety and with less chance of contamination. At the end of a procedure, the used blades can be easily accounted for by counting used units 32.

Unit 32 is inexpensive to manufacture so there is little incentive to empty blade 12 out of central chamber 34. In addition, removal of blade 12 Would obviate the advantages of the unit.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. A blade extractor and disposal unit for removing a blade from a handle having a tang, said blade having an opening therethrough and a heel abutting the handle and said tang extending upwardly through said opening to mount said blade on said tang comprising:

a substantially closed chamber formed of a semi-flexible material with a top and a bottom spaced apart a distance substantially equal to the thickness of the blade, said bottom having sides and ends and a length and width exceeding that of said blade, a groove in the bottom of the chamber that opens from one end of the bottom and has a width greater than the width of the tang and less than the width of the blade and a depth greater than the thickness of the tang at the open end of the groove, an abutment shoulder attached to the top, said abutment shoulder positioned behind the heel of the blade and extending below the plane of the bottom; and, means for increasing the distance between the top and the bottom of the chamber from the open end of the groove whereby the blade attached to the tang of the handle can be inserted into the chamber and the heel of the blade lifted from the tang and held against the abutment shoulder when the forward most end of the blade is pinched between the top and the bottom of the chamber and the tang pressed down in the groove below the plane of the bottom by manipulating the handle, the blade is then removed from the tang as the handle is pulled away from the blade with the blade remaining inside of the disposal unit.

2. The unit of claim 1 wherein the chamber is a central chamber and the means for increasing the distance between the top and the bottom of the central chamber comprises a pair of integrally formed side chambers, each of which has an open side with opposing side edges that are connected along one edge to the top of the central chamber and along opposing edges to the bottom of the central chamber, the side chambers are configured such that when they are compressed in the direction of the central chamber, the open side of the side chambers expands in length causing the distance between the top and the bottom to increase and the abutment shoulder to rise above the plane of the bottom such that a blade on a handle can be inserted into the central chamber.

3. A blade extractor and disposal unit for removing a blade from a handle having a tang, said blade having an opening therethrough and a heel abutting the handle and said tang extending upwardly through said opening to mount said blade on said tang comprising:

a flattened sleeve formed of a semi-flexible material, said sleeve having first and second ends, said sleeve closed at the first end and divided longitudinally into a central chamber flanked by two side chambers, said central chamber recessed in the sleeve at the flange end and having a top and a thickened bottom with short side flanges, said top and bottom integrally formed with the sleeve, said bottom having a length and width exceeding that of said blade, said central chamber having a distance between the top and the bottom substantially equal to the thickness of the blade and said top fitting within the side flanges of the bottom, each of said side chambers having an open side connected at one edge to the top and at a second edge to the bottom of the central chamber, said side chambers providing means for increasing the distance between the top and the bottom of the central chamber by pressing the side chambers in the direction of the central chamber, a groove in the bottom of the central chamber opening from the flange end of the sleeve and having a width greater than the width of the tang and less than the width of the blade and a depth greater than the thickness of the tang at the open end of the groove, an abutment shoulder attached to the top, said abutment shoulder positioned behind the heel of the blade and extending below the plane of the bottom, whereby the blade attached to the tang of the handle can be inserted into the central container opened by pressing on the side chambers and the heel of the blade lifted from the tang and held against the abutment shoulder when the forward most end of the blade is pinched between the top and the bottom of the central chamber and the blade flexed in the chamber by pressing the tang at the open end of the groove below the plane of the bottom by manipulating the handle, the blade is then removed from the tang as the handle is pulled away from the blade with the blade remaining inside of the disposal unit.

4. The unit of claim 3 wherein the side chambers are triangular.

5. The unit of claim 4 wherein the second end of the sleeve has a flange.

6. The unit of claim 5 wherein the recess in the central chamber has sidewalls that are laterally convergent and dimensioned to receive the handle, said sidewalls are also asymmetric so that the heel of the blade rests on shoulders formed by portions of the bottom around the groove.

7. The unit of claim 6 wherein the abutment shoulder is set at an angle complementary to the heel of the blade.

* * * * *